(12) United States Patent
Chen et al.

(10) Patent No.: US 9,150,473 B2
(45) Date of Patent: Oct. 6, 2015

(54) METHOD FOR PRODUCING ALLYL ALCOHOL

(71) Applicant: Dairen Chemical Corporation, Taipei (TW)

(72) Inventors: Shien-Chang Chen, Taipei (TW); Tian-Yuan Lin, Taipei (TW); Shih-Bo Hung, Taipei (TW)

(73) Assignee: Dairen Chemical Corporation, Taipei (TW)

( * ) Notice: Subject to any disclaimer, the term of this patent is extended or adjusted under 35 U.S.C. 154(b) by 0 days.

(21) Appl. No.: 14/221,666

(22) Filed: Mar. 21, 2014

(65) Prior Publication Data
US 2014/0364655 A1    Dec. 11, 2014

(30) Foreign Application Priority Data

Jun. 5, 2013  (TW) .............................. 102119893 A

(51) Int. Cl.
*C07C 29/09*    (2006.01)
*B01D 3/00*     (2006.01)

(52) U.S. Cl.
CPC .............. *C07C 29/095* (2013.01); *B01D 3/009* (2013.01)

(58) Field of Classification Search
CPC ...... C07C 29/095; C07C 29/80; B01D 3/0009
USPC .................................................. 568/877, 913
See application file for complete search history.

(56) References Cited

U.S. PATENT DOCUMENTS 7,041,199 B1    5/2006    Moritz et al.
8,083,903 B2    12/2011   Maruta et al.

FOREIGN PATENT DOCUMENTS

JP        60-237032        11/1985

OTHER PUBLICATIONS

English abstract of JP 60-237032.

*Primary Examiner* — Sikarl Witherspoon
(74) *Attorney, Agent, or Firm* — McCarter & English, LLP; Yu Lu

(57) ABSTRACT

A method for producing allyl alcohol is disclosed. The method includes steps of feeding allyl acetate and water into a reactive distillation column; performing a reaction in a reaction zone and separating a product containing allyl alcohol, acetic acid and water from the reactive distillation column. Accordingly, the method effectively enhances a conversion rate of hydrolysis for allyl acetate, simplifies the process and reduces energy consumption.

14 Claims, 2 Drawing Sheets

METHOD FOR PRODUCING ALLYL ALCOHOL

REFERENCE TO RELATED APPLICATION

This application claims foreign priority under 35 U.S.C. §119(a) to Patent Application No. 102119893, filed on Jun. 5, 2013, in the Intellectual Property Office of Ministry of Economic Affairs, Republic of China (Taiwan, R.O.C.), the entire contents of each of which Patent Applications are incorporated herein by reference.

BACKGROUND OF THE INVENTION

1. Field of the Invention

The present invention relates to methods for producing alcohol, and more particularly, to a method for producing allyl alcohol by hydrolysis.

2. Description of Related Art

Allyl alcohol is an important chemical intermediate for producing glycerol, medicines, perfumes, cosmetics, pesticides and the like. The allyl alcohol can also be used for producing chemical products such as epichlorohydrin, 1,4-butanediol, n-propyl alcohol, isobutyl alcohol and the like.

In the process for producing allyl alcohol via the hydrolysis of allyl acetate, since allyl acetate, allyl alcohol and water will generate azeotrope, water and esters will form two immiscible liquid phases. If a general distillation system is adopted, a plurality of separating columns including distillation, extraction and the like are required to remove allyl acetate from allyl alcohol. In such reaction system, a normal boiling point for each component and each azeotropic composition are listed in Table 1.

TABLE 1

| Component | Azeotropic composition wt % | Boiling point (° C.) |
|---|---|---|
| Allyl acetate/Allyl alcohol/Water | (75/9/16) Heterogeneous | 83.9 |
| Allyl acetate/Water | (84/16) Heterogeneous | 84.0 |
| Allyl alcohol/Water | (73/27) Homogeneous | 88.9 |
| Allyl acetate/Allyl alcohol | (37/63) Homogeneous | 94.8 |
| Allyl alcohol | — | 96.8 |
| Water | — | 100.0 |
| Allyl acetate | — | 104.3 |
| Acetic acid | — | 118.1 |

In 1985, Showa Denka (a Japanese company) has developed a technique for producing allyl alcohol by the hydrolysis of allyl acetate. However, a conversion rate of allyl acetate is restricted due to the reaction equilibrium and a conventional fixed bed reactor fails to convert allyl acetate completely. Japanese Patent No. 60-237032 has disclosed a technique for recovering allyl acetate by an azeotropic distillation column and the allyl acetate after recovery can be reused by a hydrolysis reactor.

U.S. Pat. No. 8,083,903 has disclosed a modification of the above technique, whereas the process still needs at least one hydrolysis reactor, an azeotropic distillation column and a subsequent separating column. Accordingly, the process proposed by U.S. Pat. No. 8,083,903 is very complicated and energy consuming. In U.S. Pat. No. 7,041,199, Sulzer Chemtech has disclosed a method for hydrolyzing carboxylates. The method comprises steps of feeding carboxylates in a pre-reactor for hydrolysis and then feeding the mixture from the pre-reactor into a reactive distillation column. In the method, at least one pre-reactor and a reactive distillation column are needed for enhancing the conversion rate for hydrolyzing carboxylates.

However, in view of the process for producing allyl alcohol by using hydrolysis of allyl esters, there still needs to provide a simplified process and an improved conversion rate of allyl esters.

SUMMARY OF THE INVENTION

The present invention provides a method for producing allyl alcohol. The method comprises steps of feeding a yield stream of allyl acetate and water or a feed stream of a mixture comprising allyl acetate and water into a reactive distillation column; performing a reaction in a reaction zone and isolating a product containing allyl alcohol, acetic acid and water from the reactive distillation column.

In one embodiment of the present invention, the product is isolated from the top of the reactive distillation column. In addition, the method can further comprise steps of delivering the product into a separating column and obtaining allyl alcohol from the top of the separating column. Further, acetic acid can be obtained from the bottom of the separating column.

In another embodiment of the method for producing allyl alcohol, the product is isolated from the top of the reactive distillation column and the acetic acid is isolated from the bottom of the reactive distillation column.

In the method of the present invention, the feed stream of allyl acetate and water or the feed stream of the mixture comprising allyl acetate and water is fed into the reaction zone of the reactive distillation column or an area below the reaction zone of the reactive distillation column.

In one embodiment, the allyl acetate and water are premixed to form the feed stream of the mixture.

According to the present invention, the feeding position of the feed stream of allyl acetate and water is determined based on the boiling point of the allyl acetate and water fed into different portions of the reaction zone. That is, if the allyl acetate is with a higher boiling point, it is fed into the top of the reaction zone and the water with a lower boiling point is fed into the bottom of the reaction zone, and vice versa. By doing so, the allyl acetate and water can be mixed completely and contact with each other in a reverse flow in the reaction zone. The boiling point of acetic acid is 118.1° C., the boiling point of allyl acetate is 104° C., the boiling point of water is 100° C., and the boiling point of azeotropic composition of water and allyl acetate is 84° C. Thus, in one embodiment, two feed streams are fed into the reactive distillation column, the feed stream with a higher boiling point is fed into the top of the reaction zone and the feed stream with a lower boiling point is fed into the bottom of the reaction zone. In spite of feeding the feed stream of allyl acetate and water or the feed stream of the mixture comprising allyl acetate and water into the reactive distillation column, it can be divided into two feed streams.

According to the present invention, a molar ratio of water to allyl acetate (water:allyl acetate) fed in the reactive distillation column is in the range of from 1 to 15.

According to the present invention, a pressure in the reactive distillation column is in the range of from 500 torr to 0.2 $kg/cm^2G$.

According to the present invention, the operating pressure in the separating column can be higher than the operating pressure in the reactive distillation column, such that a condenser at the top of the separating column and a reboiler of the reactive distillation column have heat exchange to save the energy consumption of the reactive distillation column.

According to the present invention, a temperature of the reaction zone in the reactive distillation column is in a range of from 80° C. to 120° C.

According to the present invention, an operating reflux ratio of the top of the reactive distillation column is greater than 2 to total reflux.

In the method for producing allyl alcohol according to the present invention, a reaction and a distillation are simultaneously carried out in the single reactive distillation column. The reaction is performed in the reaction zone filled with solid catalysts in the column, wherein the reaction zone has a plurality of column plates, a plurality of containers are disposed between each plate, and the solid catalyst is filled in the containers in which the reaction liquid flows through the containers and contacts the catalysts at the same time. The device of the present invention has about ten times more retention time than a conventional device using catalyst packages stuffed in a structured packing, such as Katapak-SP (Sulzer), and can effectively enhance the conversion rate. Generally, for the reactive distillation column provided with Katapak-SP packing having a height of 5 meters, the retention time for the liquids to flow through the whole packing merely takes about 1 to 2 minutes. However, when the reaction zone is provided with a plurality of column plates and a plurality of containers are disposed between the column plates, the retention time for the liquid at each column plate takes 1 to 2 minutes. If the spacing between any two adjacent plates is 500 mm, there are 11 plates to be disposed in the container with a height of 5 meters and the retention time is 10 to 20 minutes, which is ten times more than that of the Katapak-SP packing. Therefore, the conversion rate, when using the column plates, is higher than using catalyst packages stuffed in a structured packing.

Furthermore, in U.S. Pat. No. 7,041,199, it is demonstrated that the hydrolysis of methyl acetate is carried out by using a single reactive distillation column and the conversion rate is only 79.2% while the method of the present invention converts eaters almost completely. In addition, the method of the present invention controls the suitable feeding molar ratio of water to allyl acetate and the reflux amount of the reactive distillation column. Thus, allyl acetate is consumed completely in the reaction zone and the method of the present invention eliminates the subsequent recovery and disposal of the unreacted allyl acetate. Further, the solid catalyst is used so as to prevent corrosion by using an acidic liquid catalyst. Therefore, the method for producing allyl alcohol according to the present invention can apply in a continuous industrial production of allyl alcohol with lower costs.

DETAILED DESCRIPTION OF THE PREDERRED EMBODIMENTS

Figure 1:
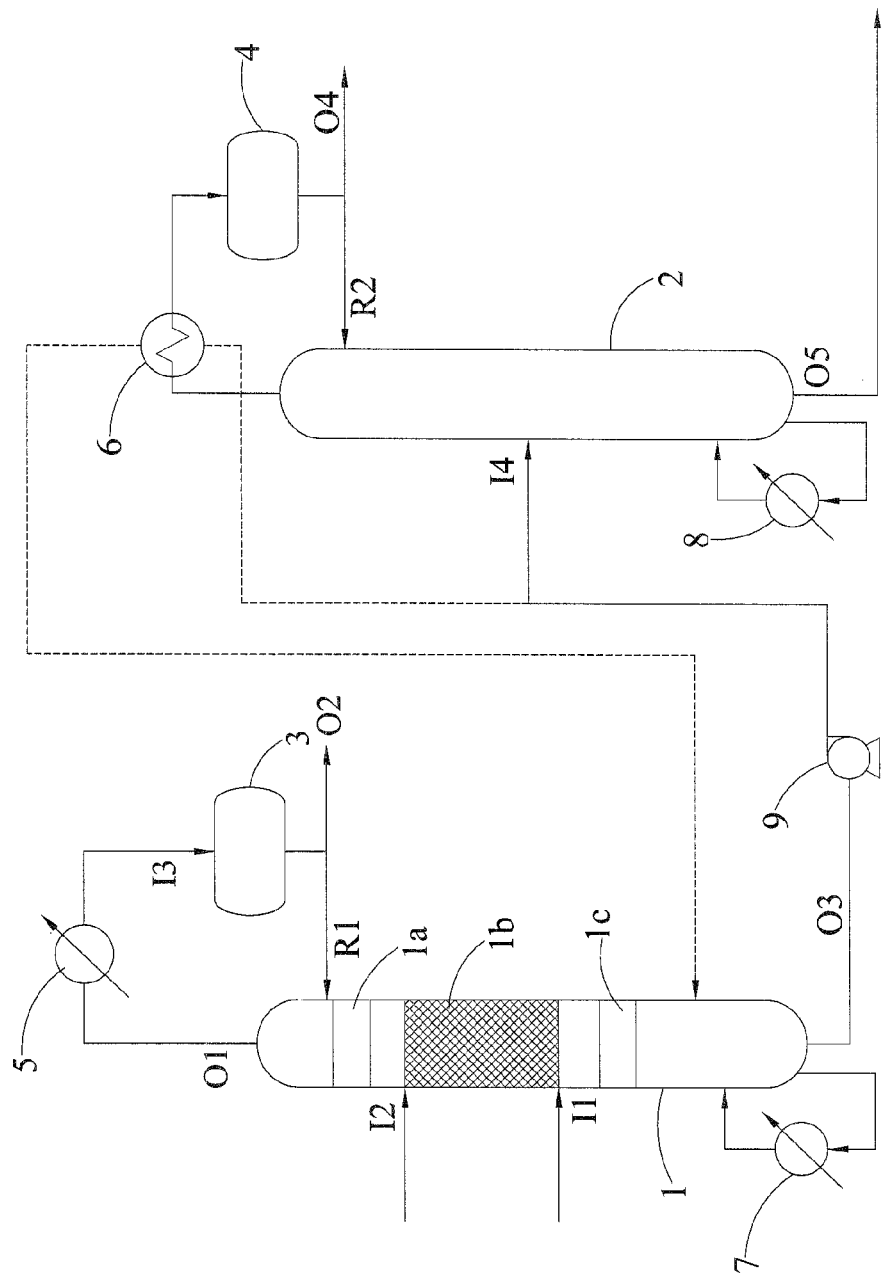
FIG. 1 shows a system for producing allyl alcohol according to the present invention, in which a reactive distillation column has two inlets in the illustrated system.

The present invention provides a method for producing allyl alcohol. The method comprises steps of feeding a feed stream of allyl acetate and water or a feed stream of a mixture comprising allyl acetate and water into a reactive distillation column; and performing a reaction in a reaction zone and separating a product containing allyl alcohol, acetic acid and water from the reactive distillation column. In the present invention, no pre-reaction is performed for the feed stream, such as the feed stream of allyl acetate and water or the feed stream of the mixture comprising allyl acetate and water.

In one embodiment of the present invention, the product is isolated from the bottom of the reactive distillation column. In addition, the method can further comprise steps of delivering the product stream into a separating column and obtaining the allyl alcohol from the top of the separating column.

In one embodiment of the present invention, the product is isolated from the top of the reactive distillation column and acetic acid is isolated from the bottom of the reactive distillation column.

In the method for producing allyl alcohol according to the present invention, the feed stream of allyl acetate and water or the feed stream of the mixture comprising allyl acetate and water is fed into the reaction zone of the reactive distillation column or an area below the reaction zone of the reactive distillation column. A rectifying section of the reactive distillation column is provided at the upper part of the reaction zone. A stripping section of the reactive distillation column is provided at the lower part of the reaction zone.

In one embodiment, the allyl acetate and water are premixed to form the mixture, before fed into the reactive distillation column.

In one embodiment, before the mixture containing allyl acetate and water is fed into the reactive distillation column, acrolein or allylidene diacetate is removed.

In the method for producing allyl alcohol according to the present invention, a reaction and a distillation are simultaneously performed in the single reactive distillation column. The reaction occurs in the reaction zone packed with solid catalysts in the column, in which the reaction zone has a plurality of column plates, a plurality of containers are disposed between the column plates and the solid catalysts are packed in the containers. The solid catalyst is an ion-exchange resin such as Purolite, DIAION SK (Mitsubishi Chemical) or Amberlyst (Dow Chemical).

According to the present invention, when the molar ratio of water to allyl acetate in the reactive distillation column is 1:1, the conversion rate is relatively high. If the allyl acetate is consumed completely in the reaction zone, it can eliminate procedures for subsequent recovery and disposal. Preferably, excess water is fed into the reactive distillation column. According to the present invention, a molar ratio of water to allyl acetate (water:allyl acetate) fed in the reactive distillation system is in the range of from 1 to 15, and preferably 2 to 15. In addition, a container having a plurality of catalyst boxes is disposed between the column plates, and the container is packed with the solid catalyst. The catalyst box contains a closed chamber and has an inlet and an outlet connected to the chamber. The container is provided with the reaction liquid flowing in and flowing out so as to provide longer retention time to consume allyl acetate.

According to the present invention, a pressure in the reactive distillation column is in the range of from 500 torr to 0.2 kg/cm$^2$G.

According to the present invention, the operating pressure in the separating column can be higher than the operating pressure in the reactive distillation column such that a condenser at the top of the separating column and a reboiler of the reactive distillation column carry out heat exchange for saving the energy consumption of the reactive distillation column. According to the present invention, temperature of the reaction zone in the reactive distillation column is in a range of from 80° C. to 120° C.

According to the present invention, an operating reflux ratio of the top of the reactive distillation column is greater than 2.

Figure 2:
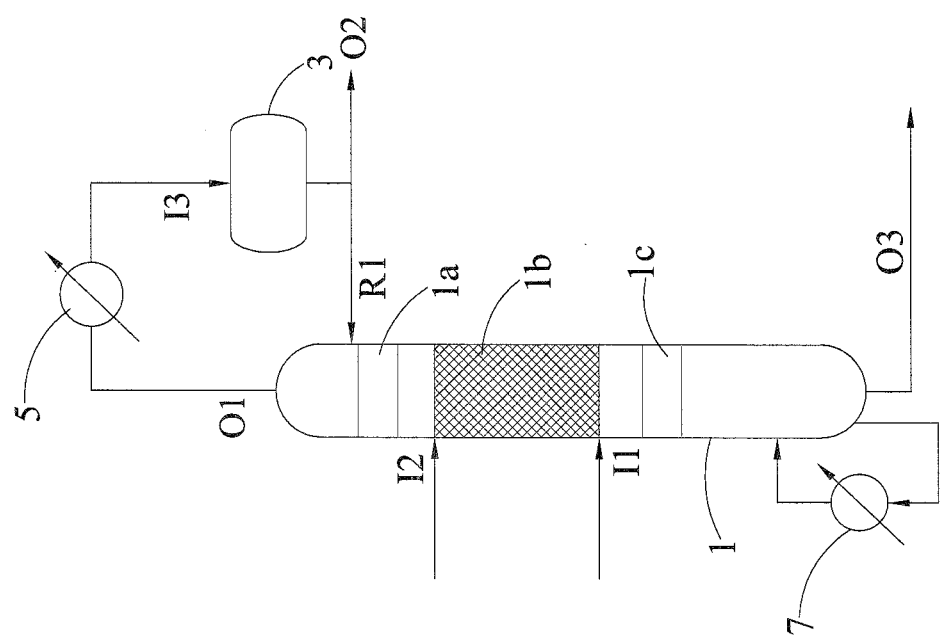
FIG. 2 shows another system for producing allyl alcohol according to the present invention.

Referred to FIG. 1 and FIG. 2, the present invention provides a system for producing allyl alcohol, in which the reactive distillation column has two inlets in the illustrated system.

As shown in FIG. 1, the system comprises a reactive distillation column 1, a separating column 2, reflux drums 3, 4, condensers 5, 6, reboilers 7, 8, and a pump 9 at the bottom of column. The reactive distillation column has a rectifying section 1a, a reaction zone 1b which is packed with solid catalysts and is disposed downstream of the recification zone 1a, a stripping zone 1c which is disposed downstream of the reaction zone, a first inlet I1, a second inlet 12, an inlet 13 of the reflux drum, an inlet R1 of the reflux, a first outlet O1, a second outlet O2 and an outlet O3 at the bottom of the reactive distillation column.

The separating column 2 has an inlet 14, a reflux inlet R2, a first outlet O4 and a second outlet O5.

The difference between the system of FIG. 1 and the system of FIG. 2 resides in that the system of FIG. 2 does not comprise the separating column 2, the reflux drum 4, the condenser 6 and the reboiler 8.

EXAMPLES

Example 1

Allyl acetate solution with water was fed into the first inlet I1 and the allyl acetate and water were hydrolyzed in the reaction zone 1b, in which the catalyst box was packed with SK 104 resin catalyst (Mitsubishi Chemical), and then a mixture containing allyl alcohol, water and acetic acid was produced from the reaction zone 1b. The reboiler 7 was disposed at the bottom of the reactive distillation column 1 and the mixture at the bottom of the reactive distillation column was heated and vaporized. The outlet of the top of the reactive distillation column was connected with the condenser 5. After most of the gas mixture was condensed in the condenser 5 and introduced into the reflux drum 3 via the inlet 13 of reflux drum, most of liquid returned to the reactive distillation column 1 via the reflux inlet R1 and a small amount of liquid was discharged from the second outlet O2 or not discharged by using the total reflux operation.

In this example, the mixture containing allyl alcohol, water and acetic acid was discharged from the outlet O3 at the bottom of the reactive distillation column. The mixture was fed into the separating column 2 from the inlet 14 by using the pump 9 at the bottom of column, or a part of liquid was delivered to the condenser 6 for heat exchange and then returned to the reactive distillation column 1 for reducing energy consumption of the reboiler 7. The allyl alcohol with water was obtained from the outlet O4 and the acetic acid with water was obtained from the outlet O5 at the bottom of the separating column.

Example 2

Example 2 was performed with the same system and condition as Example 1, except that the molar ratio of water to allyl acetate was about 1 in Example 2. Accordingly, allyl alcohol with 99.1% of purity was obtained from the outlet O4 and acetic acid with high purity was obtained from the outlet O5 at the bottom of the separating column.

Example 3

In this example, excess water was used for enhancing the conversion rate of allyl acetate. Allyl acetate solution with water was fed into the first inlet I1. Since the boiling point of water was higher than the boiling point of the mixture containing water and allyl acetate, the excess water was fed into the second inlet 12, both of water and allyl acetate contact at a reverse flow in the reaction zone and then the hydrolysis was performed to produce the mixture containing allyl alcohol, water and acetic acid. The mixture containing allyl alcohol was obtained from the second outlet O2. The mixture containing acetic acid was obtained from the outlet at the bottom of the reactive distillation column.

Results of the examples are shown in Table 2.

TABLE 2

| | | Example 1 | Example 2 | Example 3 |
|---|---|---|---|---|
| Allyl acetate feeding | Composition (wt %) | Water: 42.9% Allyl acetate: 33.0% Acetic acid: 23.8% Azeotrope: 0.3% | Water 15.4% Allyl acetate 84.6% | Water: 42.9% Allyl acetate: 33.0% Acetic acid: 23.8% Heavy azeotrope: 0.3% |
| | Feeding amount | 102.7 ton/hour | 40.1 ton/hour | 102.7 ton/hour |
| | Molar ratio of water/allyl acetate | 7.2 | 1.01 | 11 |
| Feeding amount of water | | — | — | 23.4 ton/hour |
| Total theoretical plate number | | 40 | 40 | 40 |
| Theoretical plate number of reaction zone | | 10 | 10 | 32 |
| Temperature of reaction zone | | 76 to 84° C. | 78 to 81° C. | 82 to 94° C. |
| Pressure of the top of reactive distillation column | | 500 torr | 500 torr | 500 torr |
| Reflux ratio | | Infinite reflux | Infinite reflux | 4.9 |
| Temperature of reboiler | | 92.3° C. | 102° C. | 97° C. |
| Composition of the outlet at the top of the reactive distillation column (wt %) | | — | — | Allyl alcohol 70.5% Water 29.4% Allyl acetate 0.1% |
| Composition of the outlet at the bottom of the reactive distillation column (wt %) | | Allyl alcohol 19.1% Water 36.9% Acetic acid 43.6% Allyl acetate 0.07% Heavy ends 0.34% | Allyl alcohol 48.9% Water 0.14% Acetic acid 50.7% | Allyl alcohol 70 ppm Water 54.1% Acetic acid 45.6% Heavy ends 0.3% |

TABLE 2-continued

|  | Example 1 | Example 2 | Example 3 |
|---|---|---|---|
| Theoretical plate number of separating column | 35 | 35 | — |
| Pressure of separating column | 2 kg/cm$^2$G | 2 kg/cm$^2$G | — |
| Temperature of the bottom of separating column | 127.3° C. | 159° C. | — |
| Composition of the outlet at the top of the separating column (wt %) | Allyl alcohol 72.5% Water 27.2% Allyl acetate 0.3% | Allyl alcohol 99.1% Water 0.3% Allyl acetate 0.7% | — |
| Composition of the outlet at the bottom of the separating column (wt %) | Allyl alcohol 50 ppm Water 40.4% Acetic acid 59.1% Heavy ends 0.4% | Allyl alcohol 0.1% Acetic acid 99.9% | — |

According to the present invention, in the product stream, the amount of allyl acetate is in the range of 0.1 wt % to 0.7 wt %, and it is clear that the method of the present invention enhances the conversion rate significantly.

While some of the embodiments of the present invention have been described in detail in the present, it is, however, possible for those of ordinary skill in the art to make various modifications and changes to the particular embodiments shown without substantially departing from the teaching and advantages of the present invention. Such modifications and changes are encompassed in the spirit and scope of the present invention as set forth in the appended claim.

What is claimed is:

1. A method for producing allyl alcohol, comprising steps of:
   feeding a feed stream of allyl acetate and water or a feed stream of a mixture comprising allyl acetate and water into a reactive distillation column, wherein no pre-reaction is performed for the feed stream;
   performing a reaction of the allyl acetate and water in a reaction zone of the reactive distillation column; and
   separating a product containing allyl alcohol, acetic acid and water from the reactive distillation column, wherein the reaction zone has a plurality of column plates, a plurality of containers are disposed between each of the column plates and a solid catalyst is filled in the containers.

2. The method of claim 1, wherein the product is isolated from a bottom of the reactive distillation column.

3. The method of claim 1, further comprising steps of delivering the product into a separating column and obtaining the allyl alcohol from a top of the separating column.

4. The method of claim 3, wherein a pressure in the separating column is higher than a pressure in the reactive distillation column.

5. The method of claim 1, wherein the product is isolated from a top of the reactive distillation column and the acetic acid is isolated from a bottom of the reactive distillation column.

6. The method of claim 1, wherein the allyl acetate and water are pre-mixed to form the mixture.

7. The method of claim 1, wherein the feed stream of the allyl acetate and water or the feed stream of the mixture comprising the allyl acetate and water is fed into the reaction zone of the reactive distillation column or an area below the reaction zone of the reactive distillation column.

8. The method of claim 1, wherein acrolein or allylidene diacetate is removed before feeding the feed stream of the mixture comprising the allyl acetate and water into the reactive distillation column.

9. The method of claim 1, wherein two of the feed streams are fed into the reactive distillation column, one of the two feed streams with a higher boiling point is fed into a top of the reaction zone and the other one of the two feed streams with a lower boiling point is fed into a bottom of the reaction zone.

10. The method of claim 1, wherein the solid catalyst is an ion-exchange resin.

11. The method of claim 1, wherein a molar ratio of the water to the allyl acetate is in a range of from 1 to 15.

12. The method of claim 1, wherein a reflux ratio of the reactive distillation column is from greater than 2 to total reflux.

13. The method of claim 1, wherein a pressure in the reactive distillation column is in the range of 500 torr to 0.2 kg/cm$^2$G.

14. The method of claim 1, wherein a temperature of the reactive distillation column is in a range of from 80° C. to 120° C.

* * * * *